United States Patent [19]

Kubein-Messenburg et al.

[11] Patent Number: 4,875,857
[45] Date of Patent: Oct. 24, 1989

[54] METHOD FOR RECONSTRUCTION OF TEETH IN AN UPPER JAW

[76] Inventors: Dietmar Kubein-Messenburg, Rodetal 36, 3406 Bovenden; Georg Meyer, Emilienstr. 11, 3400 Gottingen; Wolfram Bücking, Buchweg 14, 7988 Wangen, all of Fed. Rep. of Germany

[21] Appl. No.: 227,485
[22] Filed: Aug. 1, 1988

Related U.S. Application Data

[63] Continuation of Ser. No. 935,453, Nov. 26, 1986, abandoned.

[30] Foreign Application Priority Data

Nov. 29, 1985 [DE] Fed. Rep. of Germany ....... 3542177

[51] Int. Cl.$^4$ ............................................. A61C 11/00
[52] U.S. Cl. .......................................... 433/56; 433/55; 433/59; 433/62; 433/72; 433/75
[58] Field of Search .................... 433/54, 55, 56, 57, 433/58, 59, 61, 62, 63, 64, 65, 67, 68, 69, 72, 75

[56] References Cited

U.S. PATENT DOCUMENTS

| | | | |
|---|---|---|---|
| 1,228,667 | 6/1917 | Gysi | 433/57 |
| 2,200,058 | 5/1940 | Chott | 433/59 |
| 3,206,852 | 9/1965 | Swanson | 433/56 |
| 3,421,225 | 1/1969 | Stuart | 433/59 |
| 3,423,834 | 1/1969 | Irish | 433/56 |
| 4,460,339 | 7/1984 | Casper | 433/214 |
| 4,504,226 | 3/1985 | Gordon | 433/63 |

FOREIGN PATENT DOCUMENTS 845235 7/1952 Fed. Rep. of Germany ........ 433/55

Primary Examiner—John J. Wilson
Attorney, Agent, or Firm—Helfgott & Karas

[57] ABSTRACT

A method and device for reconstruction of teeth in an upper jaw wherein anterior guidance of the natural state is achieved even when front teeth are missing through the scanning of the contour curve of a tooth in the sagittal plane and the transferring by copying of the curve to each tooth to be reconstructed.

31 Claims, 5 Drawing Sheets

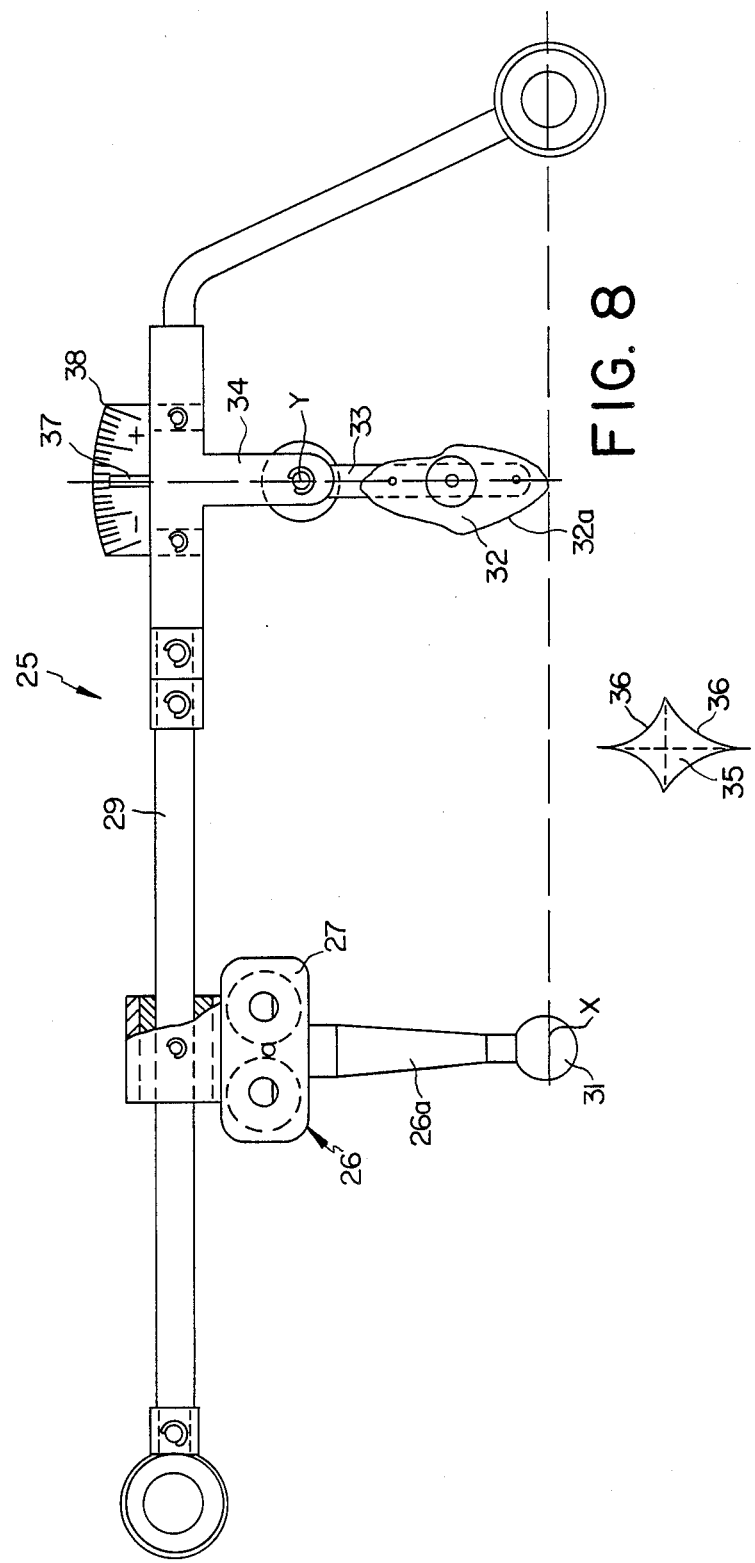

METHOD FOR RECONSTRUCTION OF TEETH IN AN UPPER JAW

This is a continuation application of Ser. No. 935,453, filed Nov. 26, 1986, now abandoned.

The present invention relates to a method for reconstruction of teeth in an upper jaw, wherein the pattern impressions of the upper and lower jaw without the tooth or teeth to be reconstructed are mounted in their natural relation to the articulations (condyles) to the skeletal skull structures, preferably in an articulator, and the teeth to be reconstructed are modeled.

In the reconstruction of teeth, a very wide variety of methods may be employed. Ordinarily, first an impression of the upper and lower jaw of the patient to be treated is taken and used to make a plaster model of the upper and lower jaw. This is then placed in an articulator, so that various movements can be executed in the model, so that a required prosthesis, as for example, crowns, complete or partial prosthesis or the like, may be adapted to the patient's special requirements beforehand in the plaster model, and the teeth to be replaced can be modeled accordingly.

Difficulties arise, however, when teeth no longer present must be reconstructed. This is the case especially with missing front teeth of the upper jaw, since the space coordinates for individual determination of the movements of the lower jaw are lacking. Ordinarily, using say an articulator according to German Patent No. 3,135,122, an incisal guide stage covered with a moldable composition is introduced with the aid of a supporting pin, the parts of the articulator being moved relative to each other and the teeth providing the requisite guidance. But if the front teeth of the upper jaw are missing, the anterior guidance is lost, and the stage cannot be introduced. To reconstruct the teeth, then, more or less trial and error is unavoidable, and this is extremely time consuming, since the prosthesis must be installed in the mouth, and only then can it be verified whether the prosthesis meets the special requirements of anterior guidance. As a rule, the prosthesis must be thus installed and removed several times, and the final result achieved often leaves much to be desired. A program of multidimensional measurement of jaw movements, say according to German Patent No. 3,123,526, is not of much help either when front teeth of the upper jaw are missing, since the anterior guidance cannot be determined in that case.

The object of the present invention is to provide a method and a device whereby it is possible to remodel the front teeth individually in such a way as to achieve an anterior guidance like that which was present in the natural state, and this even if the front teeth of the upper jaw are no longer present. At the same time, this method is to be operable by simple means, in particular with the aid of an articulator of simple design, with which the natural chewing action of the patient to be treated can be individually simulated in the jaw model.

According to the invention, a protrusive contour curve of an existing tooth of the model impression of the jaw, is taken in the sagittal plane thereof by scanning that tooth and that contour is transferred by means of a copying mechanism to the front tooth to be replaced in its sagittal plane starting from the point of contact of the front teeth of the lower jaw with the teeth of the upper jaw, to form its palatal, concavely curved surface. The invention is thus based on the discovery that the protrusive contour curves of the teeth of an individual, as found in sagittal vertical sections of the upper and lower jaw, recur in like manner for all the teeth, so that it is possible, even if the front teeth are entirely lost, to produce the palatal surface of the front teeth to be replaced by scanning the existing teeth in accordance with the method of the invention, in such manner that an anterior guidance like that present in the natural state is restored.

An alternative procedure according to the invention is that, to model the front teeth to be reconstructed in the upper jaw, the curve of the path of articulation of the condyle is scanned and transferred by means of a copying mechanism, after reduction by a factor of from 4.5 to 8.5, preferably from 5 to 7, to the front tooth to be replaced in its sagittal plane starting from the point of contact of the front teeth of the lower jaw with the teeth of the upper jaw to form its palatal, concavely curved surface. This procedure according to the invention is based on the further discovery that the curved line of the path of articulation of the condyle and the protrusive contour curves measured in the sagittal plane of an existing tooth, in accordance with the biomechanical coupling of front tooth and hinge action, are transformable into each other. In view of this discovery, therefore, it is possible by the method of the invention to achieve an exact anterior guidance in the region of the front teeth by appropriate conformation of the palatal concave curvature of the front teeth of the upper jaw even when no original teeth whatsoever remain.

To achieve the complete three-dimensional shaping of the palatal concave aspect of the front teeth of the upper jaw, it is expedient further, according to the invention, that the copying tool should be guided along the line connecting the points of contact of the front teeth of the lower jaw with the teeth of the upper jaw.

In further accordance with the invention, it is advantageous that the protrusive contour curve, or the curve of the path of articulation of the condyle as the case may be, should be taken off by means of a gauge whose form is determined by the equation of a catenary of the form $y = a \cosh(x/a) - a$, where $1 \leq a \leq 6$, preferably $2 \leq a \leq 3$, in the tooth region, or $4.5 \leq a \leq 52$, preferably $9 \leq a \leq 25$, in the hinge region.

Here the invention proceeds from the principle that the protrusive contour curve of the teeth measured in the sagittal plane as well as the shape of the path of articulation of the condyle can be exactly described by the above mentioned catenary. The factor a depends on the individual morphological particulars of the natural tooth.

In this, the invention is based on the discovery that for a factor a in the range from 1 to 6, 100% of all possible contour curves of the teeth, or, increased 4.5- to 8.5-fold, all curves of the paths of articulation, can be encompassed. Now inasmuch as, according to the invention, a gauge can be employed that encompasses the possible catenaries with factors from 1 to 6, by scanning the teeth with such a gauge the particular individual curve is easily determined, without requiring any complicated measuring procedures. In the hinge region, the same applies, with curves enlarged 4.5- to 8.5-fold.

The scanned path of articulation of the condyle is transferred to the palatal contour of the front teeth according to the following function (formula 1)

$$a^2 = \left( \frac{\sin^2 22°}{2(1 + \cos 22°)} - \frac{1 - \cos 22°}{1 + \cos 22°} \sin^2 \alpha \right) r^2$$

where r is the radius of curvature of the path of articulation and α is the initial angle of inclination to the function plane, and the variation of the range of swing is 22°±5°. In this way, the coupling between joint curvature and front tooth curvature is given exactly.

Furthermore, in this way pathological changes in the path of articulation may for example be identified, since it is ensured that curves not pathologically modified are employed for reconstruction of the teeth. On the basis of the above discovery, it is likewise possible to prefabricate the hingeing of the articulator, the so-called condyle "boxes", and likewise the other guidance elements, in accordance with the gauge in various models corresponding to the factor a=4.5 to 52, so that these elements also may be installed in the articulator in accordance with individual requirements. To carry out the procedure according to the invention, it is essential that the scanning of the protrusive contour curves in the sagittal plane of the teeth be performed in each instance on impressions with front and back teeth oriented in accordance with the ideal dental arch only.

The invention relates further to a device for practicing the method of the invention. Here the articulator is preferably so constructed that besides that axis of swing determined by the condyle boxes, at least a third bearing system is provided, so constructed that when the two articulator parts are moved adjacently, a common limiting motion corresponding to nature is generated on the part of the teeth and joints. Conventional articulators may be so used, merely to be supplemented with the third bearing system.

The latter is preferably arranged adjustable with respect to the axis of swing, and should be adjustable vertically as well. The adjustability is required so that the bearing system can be brought into a position preassigned for the particular patient. The bearing system consists of two bearing parts, one exhibiting the form of the protrusive contour curves of the teeth. The bearing part cooperating therewith may comprise a simple scanning pin, corresponding in function to the incisor edge of the lower bite. This bearing system accordingly simulates the function of the front teeth.

The contour curves of this bearing part preferably correspond to a catenary curve of the form $y = a \cosh(x/a) - a$ for $1 \leq a \leq 6$. This is determined for the particular patient to be treated individually by the parameter a.

The bearing part is preferably replaceable, so that the articulator may be adapted to other patients by simple means.

Expediently, the bearing part is swingable about a horizontal axis parallel to the axis of swing of the lower jaw, so that it may be moved into the required position.

As the condyle boxes, preferably a stirrup capable of swinging about the axis generated by them is provided, facilitating the disposition of the bearing part. This stirrup is preferably removable, so as not to obstruct access to the jaw model.

Expediently, the third bearing system is located on the centerline of the articulator or the jaw model. In this way, besides the motion of protrusion, lateral and rotary motions can be executed with fidelity to nature as well.

Preferably the upper part of the articulator is furnished with the incisal guide stage, and the corresponding lower part with a support pin. In this way, the intruded guide stage corresponds in form to the protrusive guidance contour of the front teeth. The support pin may expediently be provided with a transverse stirrup matching the dental arch for insertion, so that when the guidance stage is advanced, a three-dimensional guide surface is generated at the guidance stage by the two-dimensional protrusive motion alone.

The motions of the two articulator parts relative to each other may be motorized. In this way, a computer-controlled model of the motions of the jaws can be produced.

It is especially advantageous to provide a bridge resting in the condyle boxes on the upper part of the articulator, on which bridge is arranged a feeler, freely displaceable in two mutually perpendicular directions, for determining the protrusive contour curves of the teeth. The plane of action of the said feeler is determined firstly by the hinge axis of the articulator and secondly by the points of inflection of the protrusive guidance contour of the front teeth. In this way the feeler is always properly guided, so that the contour curves are easily determined by its means. At the end of the feeler, preferably a sensor element is provided, conveniently replaceable and affording various contour curves. The curves are determined in simple manner by applying a gauge to a tooth and comparing the curve of the gauge with that of the tooth. By comparison of the gauge with the sensor element, the curve can be traced very quickly and easily in this way. With the aid of the selected sensor element, the contour curve may be transferred as well to the tooth to be reconstructed. This arrangement may be conveniently adapted to several articulators, differing in width in the conventional manner. Also, an adaptation of the bearing system to various condyle boxes is conceivable.

The sensor element may be replaced by a machine tool, as for example grinding or milling means, themselves having the shape of the contour curves or generating them by appropriate control, so that the contour curves may likewise be transferred to nonelastic materials. All actions may be motorized, for example under the control of a computer.

Advantageous embodiments of the invention will be illustrated in detail in the course of the description to follow, with reference to the accompanying drawings, in which FIG. 1 shows a schematic representation of a lower jaw, illustrating the position of the front teeth, FIG. 2 shows a section through a front tooth, with a superposed family of curves ($y = a \cosh(x/a) - a$), FIG. 3 shows a family of curves comprised of catenaries, FIG. 4 shows a side view of an articulator according to the invention, with jaw model in place, FIG. 5 shows a side view of the third bearing system according to the invention, in partial section, FIG. 6 shows a side view of a support pin, furnished with a transverse stirrup corresponding to the dental arch, FIG. 7 shows a top view of the support pin of FIG. 6, FIG. 8 shows a side view of a scanning means according to the invention, cooperating with the upper part of an articulator.

FIG. 9 shows a side view of a gauge according to the invention, and

Figure 1:
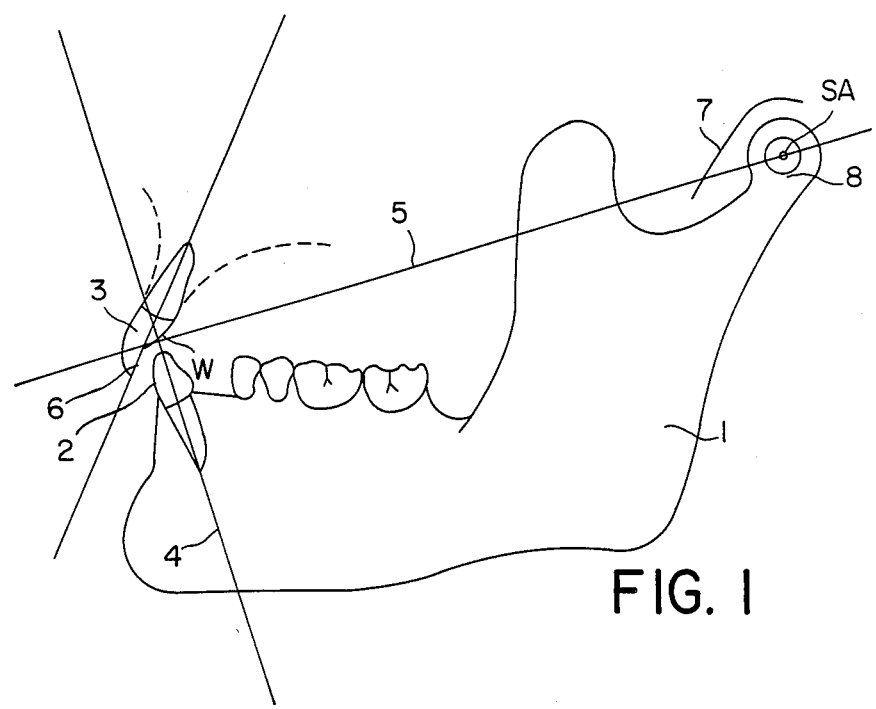

FIG. 1 schematically shows a lower jaw with front tooth 2 and a front tooth 3 of an upper jaw (not shown). These front teeth are here drawn in their ideal position. The lower front tooth 2 is so oriented that its longitudinal axis 4 is perpendicular to a straight line 5 drawn from the top edge of the front tooth 2 through a point of articulation SA in the joint (condyle). This line 5 is at the same time the tangent at the point of inflection to the protrusive guide contour 6 with its palatal concave curvature 6 of the upper front tooth 3. The contour 6 corresponds to the path of articulation 7 of the condyle 8, as converted by the formula (1) given above. To these given particulars, the articulator is to be adapted, as is about to be described.

The proper joint-related placement of the bite model in the articulator is known per se and therefore needs no further explanation.

The articulator 9 is of conventional type for the most part, so that no detailed description is required here. It has a bottom part 10 to receive the lower jaw model 11 and an upper part 12 to receive an upper jaw model 13. The parts 10 and 12 are connected together by joints, i.e. by condyle boxes 14.

In the present articulator 9, in front of an axis of swing 15 formed by the condyle boxes 14, more or less in the front teeth of the jaw model, a third bearing system 16 is provided. This bearing system 16 essentially simulates the function of the upper front teeth 3.

The bearing system 16 is composed essentially of two parts 17 and 18. The bottom part 17 is arranged on the base 10 of the articulator. It may conveniently be arranged displaceably on the bottom part, so that the point of bearing may be brought into the correct position for the jaw model in question. In this position, the bearing part 17 is disposed at the same height and in the same spatial depth referred to the axis of the swing of the articulator as the lower front tooth 2. The extreme top of the bearing part 17 thus corresponds to the upper edge of the front tooth 2.

The part 18 cooperating with part 17 is likewise slidably arranged on the top part 12 of the articulator. It is likewise vertically adjustable, so that the part 18 may be brought to the same height as the upper front tooth 3. In addition, the top part 18 is able to swing about a horizontal axis 19 parallel to the hinge axis. The part 18 may thus be swung into a position corresponding to the upper front tooth 3.

As was already clear in FIG. 1, the tangent 5 to the protrusive guide contour 6 at the point of inflection is of special significance because it must pass through the point of articulation SA of the hinge joint 8. So that the bearing part may be adjusted accordingly in simple manner, a stirrup 20 capable of swinging about the axis 15 is provided on the condyle boxes 14.

Part 18 is provided at the lower end with a curved bearing surface 18a corresponding to the protrusive guide contour 6 of the upper front tooth 3. Part 18 is to be so oriented that the bearing surface 18a merges with the straight line 5 tangentially at the apex of its guidance curve.

Since the plane of the stirrup 20 also lies on the straight line 5, the adjustment of part 18 may be effected by swinging it until its stands perpendicular to the stirrup 20. A prerequisite here is that guide contour 6 be correspondingly applied in the bearing part 18. To further facilitate the adjustment, stops 21 are provided on part 18 and/or on the stirrup 20. After adjusting the bearing part 18, the stirrup 20 may be removed from the articulator to facilitate access to the model.

Figure 2:
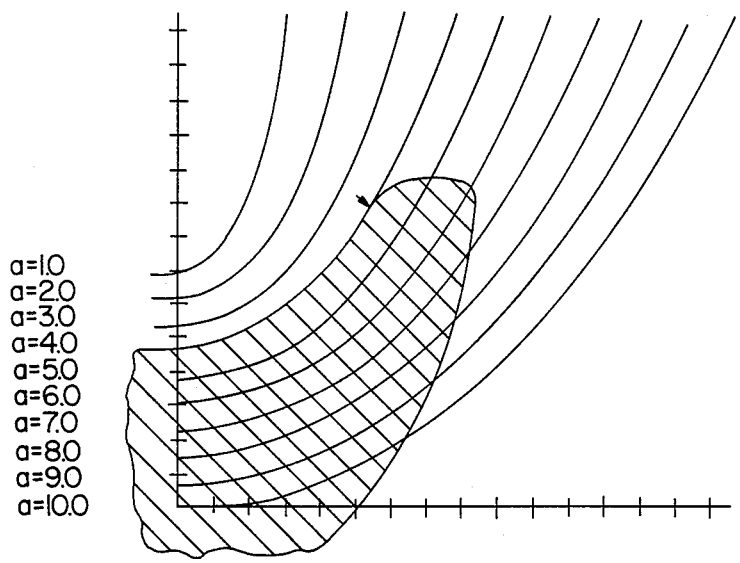
Figure 3:
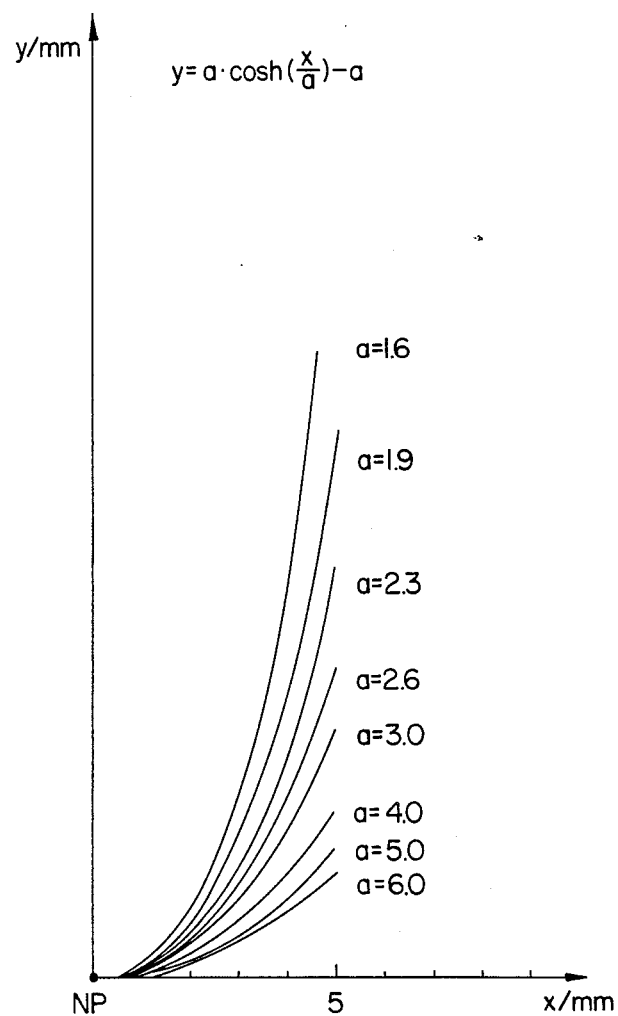
Figure 4:
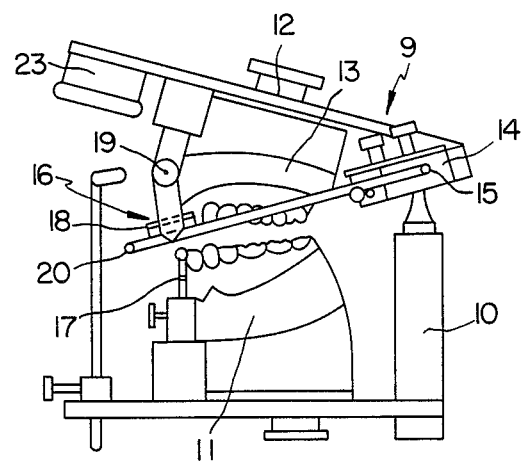
Figure 5:
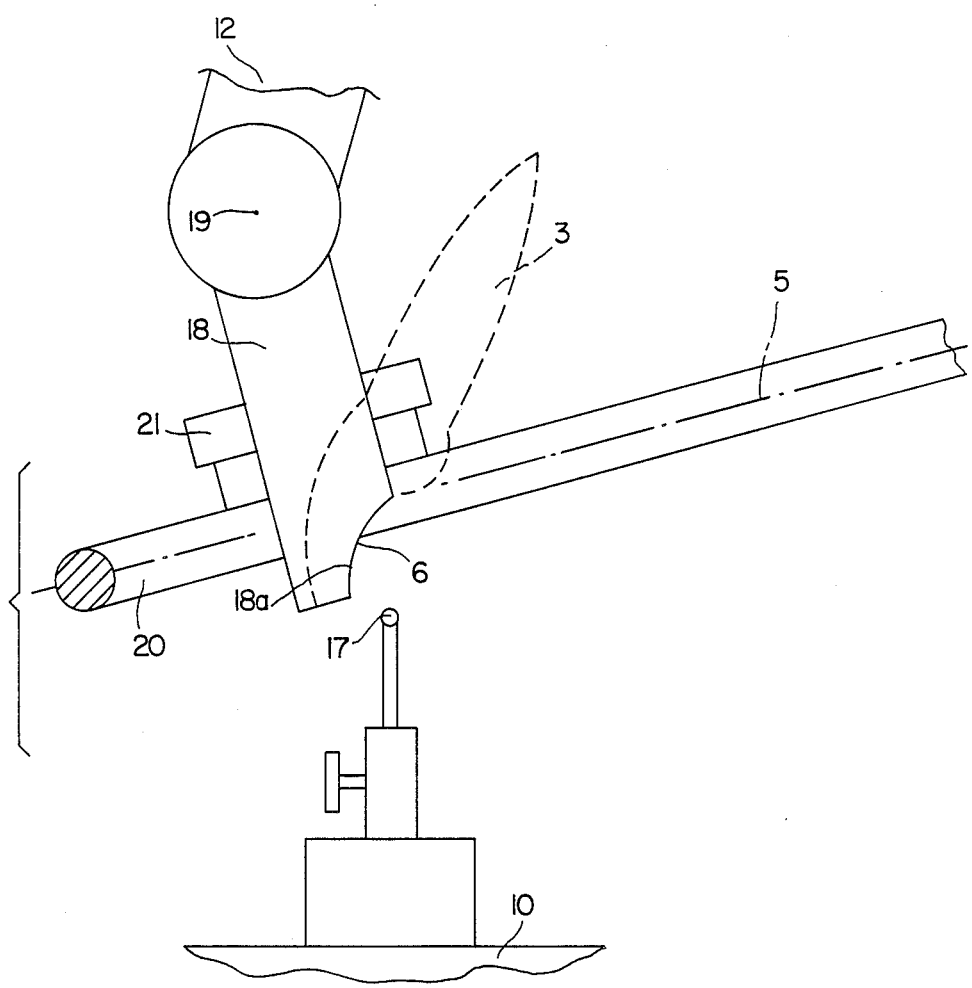
Figure 6:
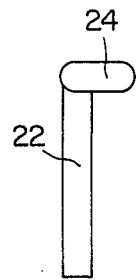
Figure 7:
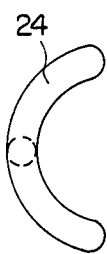

When adjusting the articulator, the procedure is to be such as to determine the protrusive guide contour 6 of the teeth. This may be done for example with the aid of sagittal vertical sections in special locations, i.e. in the front tooth region, more or less arbitrarily, and in the lateral tooth region by way of the vertices of the protuberances, namely buccally in the lower jaw and palatally in the upper jaw, in each instance at the protrusive guide contours through the bite model, starting from the vertices of the protuberances. These measured curves may then be enlarged. The resulting curve may then be determined individually by means of a prepared family of curves, more or less as represented in FIG. 2. It is to be noted that for this purpose the sections through any desired tooth may be used, since the curves repeat themselves alike on all teeth of the same individual. Using the family of curves found, a suitable bearing part 18 and at the same time a suitable condyle box 14, or a suitable adjustment of such a box, may now be selected. As previously stated, there is a fixed mathematical relationship between the condyle path 7 and the protrusive guide curve 6. Hence the form of the teeth determines the form of the articulation, depending on their spatial coordination.

The family of the curves is preferably comprised of catenary curves of the form $y = a \cosh(x/a) - a$. The curves thus differ individually in the tooth region by only a single parameter "a." In the hinge region, initially a linear portion may be included. If parabolas were chosen, for example, there would be several parameters, rendering the selection of part 18 far more complicated. After the appropriate joint parts have been installed in the articulator 9, with the bearing system 16 corresponding to the front tooth guidance, the guide stage 23, loaded with a self-setting molding compound, may be introduced in manner known per se. In so doing, the procedure is such that a protrusive movement is executed with the articulator 9. This motion is determined by the guide contour 18a of part 18. It lies in one plane only, and is consequently two-dimensional. Owing to the special construction of the support pin 22, a curved surface results in the guide stage 23, or in the moldable composition, corresponding to the guide contour 6 of the front teeth. The support pin 22 is provided for this purpose with a stirrup 24 at its upper end, formed to match the dental arch. After the molding compound has set, the bearing system 16 may be removed, so that the articulator may be utilized in known manner. Here the support pin 22 with stirrup 24 must henceforth be replaced by support pin 22 with a ball corresponding to the sagittal radius of the stirrup 24. Here it is to be noted that the form of the guide stage may be established even if no front teeth or no teeth whatever remain.

With the articulator properly adjusted, common limiting motions true to nature may now be executed with the teeth and hinge joints, since both the articulation (condyle box) and the anterior guidance correspond to the natural situation.

If the bearing system 16 is disposed on the centerline of the articulator 9, lateral motions and rotations of the jaws in relation to each other may likewise be executed true to nature.

The faithful simulation of natual movements with the articulator is of great importance, since the front teeth to be reconstructed in the upper jaw are ordinarily modeled on the bite model. The palatal surfaces of the front teeth of the upper jaw may thus be individually reproduced functionally correct in all three dimensions, as has not been possible heretofore. This is especially important when missing front teeth are to be reproduced.

The motions of the articulator may be motorized, in particular under the control of a computer. In this way a bite model with chewing action true to the original can be produced.

Furthermore, it is possible to compare the measurements obtained, i.e. the protrusive guide path 6 and the functional path of articulation 7 of the condyle, with a computer, and detect any discrepancies.

Figure 10:
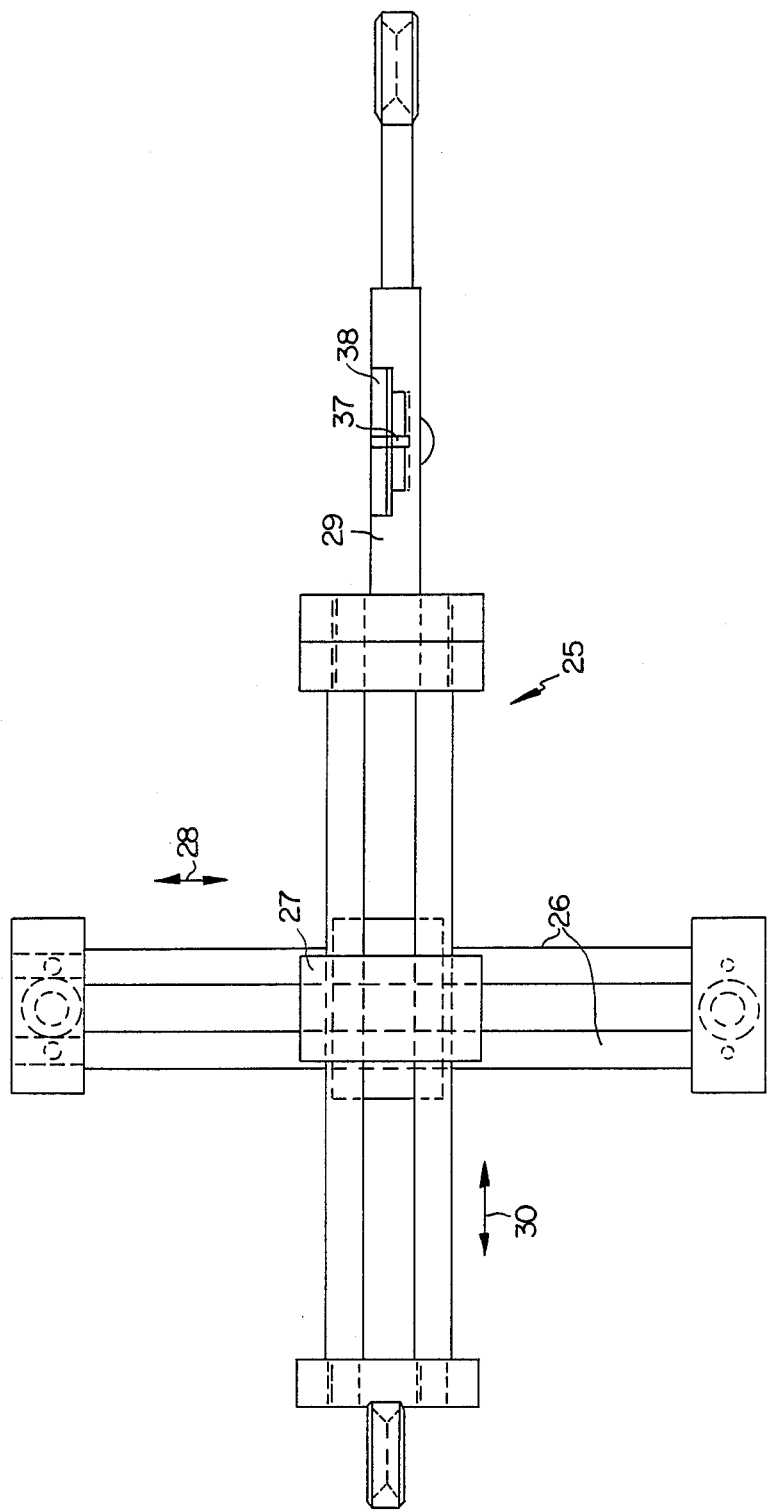
FIG. 10 shows a top view of the scanning system according to FIG. 8.

Another advantageous device for practicing the method of the invention is represented in FIGS. 8 to 10. This is a scanning system 25 comprising a bridge 26 borne in condyle boxes of an articulator top (not shown) by way of bearing extension 26a perpendicular to the bridge 26. On this bridge 26 a cross slide 27 is carried, freely displaceable on the bridge in the direction of the arrow 28. Perpendicular to this direction, the cross slide 27 bears a feeler 29 freely displaceable in its lengthwise direction, i.e. in the direction of the arrow 30. The feeler 29 can thus move freely in a plane. By the size and arrangement of balls 31 resting in the condyle boxes not shown, this plane of motion is determined firstly by the hinge axis 15 of the articulator and secondly by the points of inflection (W) of the protrusive contour curves 6 of the front teeth, see FIG. 1.

At the anterior end, the feeler 29 is equipped with a sensor element 32. This element 33 is composed of a plate, its edges 32a having a form matching the contour curves 6, the form of the edges being determined by the relationship $y = a \cosh(x/a) - a$, where $1 \leq a \leq 6$. This sensor element 32 may conveniently be replaceable, so that different contour curves selected from the predetermined family (see FIG. 2) may be very easily installed. The element 32 is so secured in a holder 33 that at the zero setting, the tangent at the apex of the catenary intersects the hinge axis X. The holder 33 for its part is fixed to an extension 34 of the feeler 29, capable of swinging about an axis Y, the axes X and Y being parallel to the bridge, so that in this way also an adaption to different forms of bite is possible. The holder 33 has a pointer 37 traveling in front of a scale 38 mounted on the feeler 29.

To scan the sagittal protrusive guide contours, for example on the lateral teeth, a gauge 35 according to FIG. 9 is conveniently used, its edges 36, in the embodiment shown by way of example, having four guide curves complementary to the contour curves 6. Here the procedure is that the gauge 35 is placed over the vertex of the cusp of a lateral tooth in the sagittal plane, and interchanged until one of its guide curves matches the contour of the tooth. The element 32 matching the gauge is selected and installed. With this element 32 thus selected, the particular appropriate contour curve 6 may now be transferred for example to a front tooth of the upper jaw on its palatal surface, which front tooth is ordinarily modeled in wax on the jaw model. Alternatively, however, the tool 32 may serve as a gauge directly.

To work other materials, such as metal or ceramic, a grinding or milling tool may be employed instead of the sensor element 32, its form matching the particular contour curve 6 selected. This tool is attached to the extension 34, capable of swinging about the axix Y. Here, conceivably all motions may be executed by motors under the control of a computer.

The balls 31 are replaceable, so that the scanning system 25 may be adapted to different articulators in a simple manner.

Modifications of these systems are conceivable in a great variety of ways. For example, as represented in the drawings, the bridge 26 may be composed of two parallel bars on which the cross slide 27 can travel to and fro. The feeler 29 too may likewise be composed of two parallel bars. Ball bearings may then be used to mount the cross slide. A scanning system so constructed is very simple in design and at the same time functionally very reliable, achieving a high precision.

In the embodiments shown by way of example, articulators have been used throughout to transfer the appropriate contour curves 6. However, it is likewise within the scope of the invention to simulate the exact locations of the upper and lower jaw by electronic data processing, to trace the individual sagittal protrusive contour curve electronically, and to transfer this contour curve to the palatal surface of the upper front tooth, or to lateral teeth to be reconstructed as the case may be, by means of an electronically controlled tool.

We claim:

1. A method of reconstructing front teeth in an upper jaw, comprising in combination the steps of:
    mounting model impressions of the upper and lower jaw without at least one front tooth to be reconstructed in their natural condyles in an articulator;
    defining points of contact of the upper jaw front teeth with corresponding lower jaw front teeth in said model impressions;
    scanning an existing tool in the model impression of a jaw to obtain a protrusive contour curve of said existing tooth in a saggital plane thereof; and
    transferring said protrusive contour curve of the existing tooth to said at least one front tooth to be reconstructed in the saggital plane by a copying tool starting from said points of contact of the upper jaw front teeth with the corresponding lower jaw front teeth to form a palatal concavely curved surface of said front tooth to be reconstructed and model said front tooth.

2. The method according to claim 1, wherein said copying tool is guided along a line connecting points of contact of the front teeth of the lower jaw with the front teeth of the upper jaw.

3. The method according to claim 1, wherein the protrusive contour curve is scanned by a gauge the shape of which is determined by the function of a catenary of the type $$y = a \cdot \cosh(x/a) - a,$$

where a is in the range between 1 and 6 for said protrusive contour in a tooth region.

4. The method according to claim 1, further including the steps of scanning the existing tooth to obtain a curve of a path of articulation of the condyle and transferring said curve by the copying tool to said front tooth to be reconstructed, wherein said protrusive contour curve and said curve of the path of articulation of the condyle are compared with each other with the aid of a computer to set up a joint function analysis.

5. The method according to claim 1, further including the steps of scanning the existing tooth to obtain a curve of a path of articulation of the condyle and transferring said curve by the copying tool to said front tooth to be reconstructed, wherein said protrusive contour curve and said curve of the path of articulation of the condyle are compared with each other with the aid of a computer to set up an occlusion analysis.

6. The method according to claim 1, wherein the protrusion contour curve is scanned electronically and transferred to said tooth to be reconstructed by an electronically controlled copying tool.

7. A method of reconstructing front teeth in an upper jaw, comprising in combination the steps of:
mounting model impressions of the upper and lower jaw without at least one front tooth to be reconstructed in their natural condyles in an articulator;
defining points of contact of the upper jaw front teeth with corresponding lower jaw front teeth in said model impressions;
scanning an existing tooth in the model impression of a jaw to obtain a curve of a path of articulation of the condyle; and
transferring said curve of the path of articulation to said at least one front tooth to be reconstructed in the saggital plane by a copying tool starting from said points of contact of the upper jaw front teeth with the corresponding lower jaw front teeth to form a palatal concavely curved surface of said front tooth to be reconstructed and model said front tooth.

8. The method according to claim 7, wherein said curve of the path of articulation of the condyle is transferred according to the function $$a^2 = \left( \frac{SIN^2 22°}{2.(1 + COS22°)} \cdot \frac{1 - COS22°}{1 + COS22°} - SIN^2 \alpha \right) \cdot r^2$$

wherein r is the radius of curvature of the path of articulation;
α is the initial angle of inclination to the function plane; and
22°±5° is the variation in the range of swing.

9. The method according to claim 7, wherein the curve of the path of articulation of the condyle is scanned by a gauge the shape of which is determined by the function of a catenary of the type $$y = a.COSH(x/a) - a,$$

where a is in the range between 4.5 and 8.5, in a hinge region.

10. Apparatus for reconstructing front teeth in an upper jaw, comprising an articulator representing motions of the upper and lower jaw;
means for mounting model impressions of the upper and lower jaw without at least one front tooth to be reconstructed in their natural condyles in said articulator;
means for scanning an existing tooth in the model impression of a jaw to obtain a protrusive contour curve of said existing tooth in a saggital plane thereof; and
a copying tool for transferring said protrusive contour curve of the existing tooth to said at least one front tooth to be reconstructed in the saggital plane starting from points of contact of the upper jaw front teeth with the corresponding lower jaw front teeth to form a palatal concavely curved surface of said front tooth to be reconstructed and model said front tooth;
said articulator having a bottom part corresponding to the lower jaw and a top part corresponding to the upper jaw,
said parts being interconnected by a hinge axis providing condyle box type bearings, positioned at a first location and a support pin positioned at a second location opposite to said hinge axis, and guide means operable upon motion of said parts relative to each other to provide a common limiting motion of teeth and articulations corresponding to nature.

11. Apparatus according to claim 10, wherein the guide means is patterned in accordance with the protrusive contour of the existing teeth in the model impression.

12. Apparatus according to claim 11, wherein the shape of said guide means corresponds to a catenary of the form derived from the equation $$y = a.COSH(x/a) - a$$

where a is in the range between 1 and 6.

13. Apparatus according to claim 10, wherein the guide means is disposed adjustably in relation to the hinge axis of the articulator.

14. Apparatus according to claim 10, wherein the guide means is vertically adjustable.

15. Apparatus according to claim 10, wherein the guide means comprises a guide part capable of swinging about a horizontal axis of the articulator.

16. Apparatus according to claim 15, wherein the guide means is replaceable.

17. Apparatus according to claim 15, wherein the articulator comprises a stirrup capable of swinging about the hinge axis to adjust the guide means.

18. Apparatus according to claim 10, further including a guide stage arranged on the top part of the articulator and the support pin is positioned on the bottom part of the articulator.

19. Apparatus according to claim 18, wherein the support pin is provided at its end with a stirrup corresponding to the dental arch.

20. Apparatus according to claim 19, wherein the guide stage is arranged rotatably.

21. Apparatus for reconstructing front teeth in an upper jaw, comprising an articulator representing motions of the upper and lower jaw;
means for mounting model impressions of the upper and lower jaw without at least one front tooth to be reconstructed in their natural condyles in said articulator;
means for scanning an existing tooth in the model impression of a jaw to obtain a protrusive contour curve of said existing tooth in a saggital plane thereof; and
a copying tool for transferring said protrusive contour curve of the existing tooth to said at least one front tooth to be reconstructed in the saggital plane starting from points of contact of the upper jaw front teeth with the corresponding lower jaw front teeth to form a palatal concavely curved surface of said front tooth to be reconstructed and model said front tooth;
said articulator including at a top part thereof a bridge mounted in the condyle boxes, and a feeler freely displaceable on said bridge in two mutually perpendicular directions for scanning and transferring the protrusive contour curves of the teeth.

22. Apparatus according to claim 21, wherein directions of motion of the feeler lie in a plane determined by a hinge axis of the top part of the articulator and by points of inflection of the protrusive contour curves of the front teeth of the upper jaw.

23. Apparatus according to claim 22, wherein a sensor element is provided at an end of the feeler, said sensor element having edges having a contour matching the protrusive guide curve corresponding to the form $y = a.\mathrm{COSH}\,(x/a) - a$, where a is in the range between 1 and 6.

24. Apparatus according to claim 23, wherein the sensor element is replaceable by elements having contours of different catenaries.

25. Device according to claim 23, wherein the sensor element at the end of the feeler is disposed adjustably about an axis (Y).

26. Apparatus according to claim 23, wherein the feeler is mounted in a cross slide traveling on the bridge.

27. Apparatus according to claim 26, wherein the sensor element has several edges with different contour curves and is arranged fixably.

28. Apparatus according to claim 26, wherein a lodgment of the bridge in condyle boxes is adaptable to different articulators and to different condyle boxes.

29. Apparatus according to claim 26, wherein the sensor element at the end of the feeler comprises a grinding tool.

30. Apparatus according to claim 26, wherein motions of the feeler and of the tool are motorized.

31. Apparatus according to claim 26, wherein the sensor element at the end of the feeler comprises a milling tool.

* * * * *